United States Patent
Yang et al.

(10) Patent No.: US 11,136,373 B2
(45) Date of Patent: Oct. 5, 2021

(54) FERMENTATION PROCESS FOR INCREASING PRODUCTION LEVEL OF RECOMBINANT HUMAN COLLAGEN

(71) Applicant: JIANGSU JLAND BIOTECH CO., LTD., Jingjiang (CN)

(72) Inventors: Shulin Yang, Nanjing (CN); Erfeng Du, Jingjiang (CN); Jianmin Huang, Jingjiang (CN); Lihu Gao, Jingjiang (CN); Jianfeng Zhao, Jingjiang (CN); Hai Tao, Jingjiang (CN); Liping Feng, Jingjiang (CN); Aimei Zhou, Jingjiang (CN)

(73) Assignee: JIANGSU JLAND BIOTECH CO., LTD., Jingjiang (CN)

( * ) Notice: Subject to any disclaimer, the term of this patent is extended or adjusted under 35 U.S.C. 154(b) by 340 days.

(21) Appl. No.: 16/318,556

(22) PCT Filed: Oct. 18, 2016

(86) PCT No.: PCT/CN2016/102435
§ 371 (c)(1),
(2) Date: Jan. 17, 2019

(87) PCT Pub. No.: WO2018/014453
PCT Pub. Date: Jan. 25, 2018

(65) Prior Publication Data
US 2019/0241645 A1    Aug. 8, 2019

(30) Foreign Application Priority Data
Jul. 22, 2016 (CN) .......................... 201610587403.X

(51) Int. Cl.
C07K 14/78 (2006.01)
C12N 1/16 (2006.01)
C12P 21/02 (2006.01)
C12R 1/84 (2006.01)

(52) U.S. Cl.
CPC .............. *C07K 14/78* (2013.01); *C12N 1/165* (2021.05); *C12P 21/02* (2013.01); *C12R 2001/84* (2021.05)

(58) Field of Classification Search
CPC ........ C07K 14/78; C12P 21/02; C12N 15/815
See application file for complete search history.

(56) References Cited

U.S. PATENT DOCUMENTS

| | | | |
|---|---|---|---|
| 2008/0145899 A1 | 6/2008 | Johnson et al. | |
| 2018/0237813 A1* | 8/2018 | Noda | C12P 13/22 |

FOREIGN PATENT DOCUMENTS

| | | | |
|---|---|---|---|
| CN | 10150771 | * | 11/2009 |
| CN | 102443057 A | | 5/2012 |
| CN | 103725623 A | | 4/2014 |
| CN | 104561201 A | | 4/2015 |
| WO | WO 2014/170460 A2 | | 10/2014 |
| WO | WO 2015/177800 A2 | | 11/2015 |

OTHER PUBLICATIONS

International Search Report, issued in PCT/CN2016/102435, dated Apr. 27, 2017.
Li et al., "Study on the Culture Conditions of L-lactic Acid Bacteria", Liquor-Making Science & Technology, 2007, No. 3 (Tol.153), total 5 pages.
Yin et al., "Intracellular Expression and Purification of the Canstatin-N Protein in Pichia Pastoris". Gene, 2012, vol. 504, pp. 122-126.
Çelik et al., "Metabolic Flux Analysis for Recombinant Protein Production by Pichia pastoris Using Dual Carbon Sources: Effects of Methanol Feeding Rate", Biotechnology and Bioengineering, vol. 105, No. 2, Feb. 1, 2010 (published online Sep. 23, 2009), pp. 317-329.
Cornelissen et al., "Production of Recombinant Proteins with Pichia pastoris in Integrated Processing", Eng. Life Sci., vol. 3, No. 9, Sep. 10, 2003, pp. 361-370.
Extended European Search Report dated Mar. 21, 2019 for Application No. 16909380.4.
Ren et al., "Modeling and Model Based Feeding Control for Pichia pastoris fed-batch cultivation", IFAC Advanced Control of Chemical Processes, Jan. 1, 2004, pp. 451-456.
Ma et al., "An approach for enhancing the production of human-like collagen II by enlarging the metabolic flux at pyruvate node," Pak. J. Pharm. Sci., vol. 27, No. 6, Nov. 2014, pp. 2109-2117.
Nocon et al., "Model based engineering of Pichia pastoris central metabolism enhances recombinant protein production," Metabolic engineering, vol. 24, 2014 (available online May 20, 2014), pp. 129-138.
"Pichia Fermentation Process Guidelines," Invitrogen, pp. 1-11.
Nokelainen et al., "High-level production of human type I collagen in the yeast *Pichia pastoris*," Yeast, vol. 18, 2001, pp. 797-806.

(Continued)

*Primary Examiner* — Maryam Monshipouri
(74) *Attorney, Agent, or Firm* — Birch, Stewart, Kolasch & Birch, LLP

(57) ABSTRACT

The present invention provides a fermentation process for improving the production level of a recombinant human collagen. The process comprises inoculating a sterilized fermentation medium with a Pichia yeast solution, then performing fermentation culturing for 14-18 hrs, adding methanol to induce the expression, upon which sodium pyruvate is added to the fermentation medium, wherein the amount of the sodium pyruvate added is 0.01-10 g/L. In the fermentation process of the present invention, the sodium pyruvate is added in the methanol-induced expression stage, so that the biosynthesis rate of the recombinant human collagen is improved; and a continuous feed-batch mode is adopted, so that the biosynthesis rate of the recombinant human collagen is further improved, and the fermentation time is shortened. Meanwhile, the expression level of the recombinant human collagen is increased, the fermentation level is increased by more than 20%, and the production cost is reduced. The fermentation process is especially suitable for industrialized mass production of recombinant human collagen, and is of huge practical application value in industrial production.

6 Claims, No Drawings

(56) References Cited

OTHER PUBLICATIONS

Prof. Dr. Jochen Büchs, "Zur Vorlage im Einspruchsverfahren gegen das Europäische Patent EP 3 473 726 B1 der Jiangsu Biotech Co., Ltd.," Erklärung, pp. 1-15.
Stratton et al., "High Cell-Density Fermentation," Methods in Molecular Biology, vol. 103: Pichia Protocols, 1998, pp. 107-120.
Unrean, "Pathway Analysis of Pichia pastoris to Elucidate Methanol Metabolism and Its Regulation for Production of Recombinant Proteins," Biotechnol. Prog., vol. 30, No. 1, 2014 (published online Dec. 21, 2013), pp. 28-37.

* cited by examiner

FERMENTATION PROCESS FOR INCREASING PRODUCTION LEVEL OF RECOMBINANT HUMAN COLLAGEN

TECHNICAL FIELD

The present invention relates to the technical field of bio-fermentation technologies, and to a fermentation process for increasing the production level of a recombinant human collagen.

RELATED ART

Collagen is an important class of proteins in animals, which are widely distributed in skin, cartilage, blood vessels and other tissues and involved in cell migration, differentiation and reproduction, play an important role in maintaining normal physiological functions of cells, tissues, and organs, and find wide use in food, feed, cosmetology, cosmetics, pharmaceuticals and other common areas. At present, raw materials of collagen are mainly obtained by physically or chemically treating the skin, bones and other tissues of pigs, cattle and other animals with acid, alkali, or by heating, and then separating and purifying. However, the collagen component obtained by the above method is complex, has poor water solubility, and has hidden viruses due to the animal tissue sources, which limits the use of collagen in medicine.

With the rapid development of recombinant DNA technology, various host cells are used as genetically engineered bacteria for expression of collagen. Compared with the traditional process, a fermentation process with genetically engineered bacteria of collagen has the advantages of readily available raw materials, environmental protection, stable product quality and others, but there are also problems such as long fermentation period and low production efficiency. Chinese Patent No. 201010602214.8 discloses a production method with a Pichia yeast expressing a recombinant human collagen, in which *Pichia pastoris* C13 is used as a fungal strain, the recombinant collagen expression level is 5 g/L, the fermentation period is 99 hours, and the fermentation level is 0.051 g/L·h. Although the fermentation period is short, the protein expression level and fermentation level are too low. In Chinese patent No. 201110327865.5, a genetically engineered strain of *Pichia pastoris* expressing a recombinant human collagen is constructed, which is fermentation cultured to obtain the recombinant human collagen. The fermentation period is 136 hrs, the protein expression level is 16 g/L, and the fermentation level is 0.118 g/L·h. Although the protein expression level is increased, the fermentation period is too long and the fermentation level is low. Therefore, further shortening the fermentation time, increasing the protein expression level, and increasing the fermentation level are beneficial to the industrialized large-scale production of collagen, and can bring practical application value to industrial production.

SUMMARY

An object of the present invention is to provide a fermentation process for increasing the production level of a recombinant human collagen. By adding 0.01 to 10 g/L of sodium pyruvate during the fermentation process, the growth and metabolic rate of the Pichia yeast is regulated, the fermentation period is shortened, the expression level of the recombinant human collagen is increased, and the production level of the recombinant human collagen is further increased.

The following technical solution is adopted in the present invention.

A fermentation process for improving the production level of a recombinant human collagen comprises the steps of inoculating a sterilized fermentation medium with a Pichia yeast solution, then performing fermentation culturing for 14-18 hrs, and adding methanol to induce the expression, upon which sodium pyruvate is added to the fermentation medium, wherein the amount of the sodium pyruvate added is 0.01-10 g/L.

The Pichia yeast mentioned in the present invention is *Pichia pastoris* deposited in China General Microbiological Culture Collection Center (CGMCC) under CGMCC Accession No. 5021 on Jun. 29, 2011, and fully disclosed in Chinese Patent No. 201110327865.5.

Preferably, the amount of the sodium pyruvate added is 0.1-1 g/L.

Preferably, the sodium pyruvate is added in a fed-batch mode.

The fermentation medium of the Pichia yeast described in the present invention may have a conventional composition comprising 6.6-26.7 mL/L of 85% $H_3PO_4$, 0.3-1.175 g/L of $CaSO_4 \cdot 2H_2O$, 4.5-18.2 g/L of $K_2SO_4$, 3.7-14.9 g/L of $MgSO_4 \cdot 7H_2O$, 1.0-4.13 g/L of KOH, 10.0-40.0 g/L of glycerol, and 0.435-4.35 mL/L of a PTM1 solution.

In the fermentation process of the present invention, the Pichia yeast solution is inoculated in an amount of 8-12%, the fermentation temperature is 28-30° C., the pH is adjusted to 5.0-5.2 with aqueous ammonia, the dissolved oxygen is not less than 20%, and the induction time with methanol is 90-120 hrs.

Compared with the prior art, the present invention has the following obvious beneficial effects. In the fermentation process of the present invention, the sodium pyruvate is added in the methanol-induced expression stage, so that the biosynthesis rate of the recombinant human collagen is improved; and a continuous feed-batch mode is adopted, so that the biosynthesis rate of the recombinant human collagen is further improved, and the fermentation time is shortened. Meanwhile, the expression level of the recombinant human collagen is increased, the fermentation level is increased by more than 20%, and the production cost is reduced. The fermentation process is especially suitable for industrialized mass production of recombinant human collagen, and is of huge practical application value in industrial production.

DETAILED DESCRIPTION

In a specific example of the present invention, the fungal strain used is a Pichia yeast expressing a recombinant human collagen, which is *Pichia pastoris* deposited in China General Microbiological Culture Collection Center (CGMCC) under CGMCC Accession No. 5021 on Jun. 29, 2011.

Refer to the operation manual of Invitrogen for the PTM1 solution mentioned in the present invention, which has a specific composition comprising 6.0 g/L of $CuSO_4 \cdot 5H_2O$; 0.08 g/L of NaI; 3.0 g/L of $MnSO_4 \cdot H_2O$; 0.2 g/L of $NaMoO_4 \cdot 2H_2O$; 0.02 g/L of $H_3BO_3$; 0.5 g/L of $CoCl_2$; 20.0 g/L of $ZnCl_2$; 65.0 g/L of $FeSO_4 \cdot 7H_2O$; 0.2 g/L of biotin; and 5.0 mL/L of $H_2SO_4$, sterilized by filtration through a 0.22 μm filter membrane, and stored at room temperature.

The present invention will be further described in detail below with reference to examples and accompanying drawings.

Example 1

Fermentation medium: 85% $H_3PO_4$ 26.7 mL/L; $CaSO_4.2H_2O$ 1.175 g/L; $K_2SO_4$ 18.2 g/L; $MgSO_4.7H_2O$ 14.9 g/L; KOH 4.13 g/L; glycerol 40.0 g/L; and PTM1 4.35 mL/L.

A seed culture was added to a 1000 L fermentor containing 500 L of a fermentation medium at an inoculation amount of 10%, the initial stirring speed was 200 rpm, the fermentor pressure was 0.05 MPa, and the air flow rate and the stirring speed were adjusted so that the dissolved oxygen (DO) was >30%. When the carbon source was depleted, the dissolved oxygen rose sharply. 50% glycerol was added in a fed-batch mode, and the carbon source was supplemented. The addition of glycerol was stopped when the wet weight of the fungal cells was 212 g/L. At this time, the fermentation culturing time was 16 hrs. After the glycerol was depleted, methanol was added in a fed-batch mode, the process proceeded to a methanol-induced culture stage, and sodium pyruvate was added in one portion in an amount of 0.01 g/L of the fermentation medium. The rotation speed, the air flow rate and the fed-batch addition rate of methanol were adjusted to allow the dissolved oxygen (DO) to reach >20%. After 96 hrs of induced fermentation, the fermentation was completed. The fermentation liquid was collected, and the supernatant of the fermentation liquid was obtained by centrifugation. The final concentration of the recombinant human collagen is 16.0 g/L as detected by HPLC. The fermentation period is 112 hrs, and the fermentation production level is 0.143 g/L·h, which is 23.3% higher than that of the control group.

Example 2

Fermentation medium: 85% $H_3PO_4$ 26.7 mL/L; $CaSO_4.2H_2O$ 1.175 g/L; $K_2SO_4$ 18.2 g/L; $MgSO_4.7H_2O$ 14.9 g/L; KOH 4.13 g/L; glycerol 40.0 g/L; and PTM1 4.35 mL/L.

A seed culture was added to a 1000 L fermentor containing 500 L of a fermentation medium at an inoculation amount of 10%, the initial stirring speed was 200 rpm, the fermentor pressure was 0.05 MPa, and the air flow rate and the stirring speed were adjusted so that the dissolved oxygen (DO) was >30%. When the carbon source was depleted, the dissolved oxygen rose sharply. 50% glycerol was added in a fed-batch mode, and the carbon source was supplemented. The addition of glycerol was stopped when the wet weight of the fungal cells was 210 g/L. At this time, the fermentation culturing time was 16 hrs. After the glycerol was depleted, methanol was added in a fed-batch mode, the process proceeded to a methanol-induced culture stage, and sodium pyruvate was added in one portion in an amount of 10 g/L. The rotation speed, the air flow rate and the fed-batch addition rate of methanol were adjusted to allow the dissolved oxygen (DO) to reach >20%. After 96 hrs of induced fermentation, the fermentation was completed. The fermentation liquid was collected, and the supernatant of the fermentation liquid was obtained by centrifugation. The final concentration of the recombinant human collagen is 16.8 g/L as detected by HPLC. The fermentation period is 112 hrs, and the fermentation production level is 0.150 g/L·h, which is 29.3% higher than that of the control group.

Example 3

Fermentation medium: 85% $H_3PO_4$ 26.7 mL/L; $CaSO_4.2H_2O$ 1.175 g/L; $K_2SO_4$ 18.2 g/L; $MgSO_4.7H_2O$ 14.9 g/L; KOH 4.13 g/L; glycerol 40.0 g/L; and PTM1 4.35 mL/L.

A seed culture was added to a 1000 L fermentor containing 500 L of a fermentation medium at an inoculation amount of 10%, the initial stirring speed was 200 rpm, the fermentor pressure was 0.05 MPa, and the air flow rate and the stirring speed were adjusted so that the dissolved oxygen (DO) was >30%. When the carbon source was depleted, the dissolved oxygen rose sharply. 50% glycerol was added in a fed-batch mode, and the carbon source was supplemented. The addition of glycerol was stopped when the wet weight of the fungal cells was 216 g/L. At this time, the fermentation culturing time was 17 hrs. After the glycerol was depleted, methanol was added in a fed-batch mode, the process proceeded to a methanol-induced culture stage, and sodium pyruvate was added in one portion in an amount of 0.1 g/L. The rotation speed, the air flow rate and the fed-batch addition rate of methanol were adjusted to allow the dissolved oxygen (DO) to reach >20%. After 96 hrs of induced fermentation, the fermentation was completed. The fermentation liquid was collected, and the supernatant of the fermentation liquid was obtained by centrifugation. The final concentration of the recombinant human collagen is 17.8 g/L as detected by HPLC. The fermentation period is 113 hrs, and the fermentation production level is 0.158 g/L·h, which is 36.2% higher than that of the control group.

Example 4

Fermentation medium: 85% $H_3PO_4$ 26.7 mL/L; $CaSO_4.2H_2O$ 1.175 g/L; $K_2SO_4$ 18.2 g/L; $MgSO_4.7H_2O$ 14.9 g/L; KOH 4.13 g/L; glycerol 40.0 g/L; and PTM1 4.35 mL/L.

A seed culture was added to a 1000 L fermentor containing 500 L of a fermentation medium at an inoculation amount of 10%, the initial stirring speed was 200 rpm, the fermentor pressure was 0.05 MPa, and the air flow rate and the stirring speed were adjusted so that the dissolved oxygen (DO) was >30%. When the carbon source was depleted, the dissolved oxygen rose sharply. 50% glycerol was added in a fed-batch mode, and the carbon source was supplemented. The addition of glycerol was stopped when the wet weight of the fungal cells was 213 g/L. At this time, the fermentation culturing time was 18 hrs. After the glycerol was depleted, methanol was added in a fed-batch mode, the process proceeded to a methanol-induced culture stage, and a sodium pyruvate solution was added in a continuous fed-batch mode in a total amount of 0.1 g/L until the fermentation was completed. The rotation speed, the air flow rate and the fed-batch addition rate of methanol were adjusted to allow the dissolved oxygen (DO) to reach >20%. After 90 hrs of induced fermentation, the fermentation was completed. The fermentation liquid was collected, and the supernatant of the fermentation liquid was obtained by centrifugation. The final concentration of the recombinant human collagen is 18.2 g/L as detected by HPLC. The fermentation period is 108 hrs, and the fermentation production level is 0.169 g/L·h, which is 45.3% higher than that of the control group.

Example 5

Fermentation medium: 85% $H_3PO_4$ 26.7 mL/L; $CaSO_4.2H_2O$ 1.175 g/L; $K_2SO_4$ 18.2 g/L; $MgSO_4.7H_2O$ 14.9 g/L; KOH 4.13 g/L; glycerol 40.0 g/L; and PTM1 4.35 mL/L.

A seed culture was added to a 1000 L fermentor containing 500 L of a fermentation medium at an inoculation amount of 10%, the initial stirring speed was 200 rpm, the fermentor pressure was 0.05 MPa, and the air flow rate and the stirring speed were adjusted so that the dissolved oxygen (DO) was >30%. When the carbon source was depleted, the dissolved oxygen rose sharply. 50% glycerol was added in a fed-batch mode, and the carbon source was supplemented. The addition of glycerol was stopped when the wet weight of the fungal cells was 212 g/L. At this time, the fermentation culturing time was 16 hrs. After the glycerol was depleted, methanol was added in a fed-batch mode, the process proceeded to a methanol-induced culture stage, and a sodium pyruvate solution was added in a continuous fed-batch mode in a total amount of 1 g/L until the fermentation was completed. The rotation speed, the air flow rate and the fed-batch addition rate of methanol were adjusted to allow the dissolved oxygen (DO) to reach >20%. After 96 hrs of induced fermentation, the fermentation was completed. The fermentation liquid was collected, and the supernatant of the fermentation liquid was obtained by centrifugation. The final concentration of the recombinant human collagen is 18.0 g/L as detected by HPLC. The fermentation period is 112 hrs, and the fermentation production level is 0.161 g/L·h, which is 38.8% higher than that of the control group.

Example 6

Fermentation medium: 85% $H_3PO_4$ 26.7 mL/L; $CaSO_4.2H_2O$ 1.175 g/L; $K_2SO_4$ 18.2 g/L; $MgSO_4.7H_2O$ 14.9 g/L; KOH 4.13 g/L; glycerol 40.0 g/L; and PTM1 4.35 mL/L.

A seed culture was added to a 1000 L fermentor containing 500 L of a fermentation medium at an inoculation amount of 10%, the initial stirring speed was 200 rpm, the fermentor pressure was 0.05 MPa, and the air flow rate and the stirring speed were adjusted so that the dissolved oxygen (DO) was >30%. When the carbon source was depleted, the dissolved oxygen rose sharply. 50% glycerol was added in a fed-batch mode, and the carbon source was supplemented. The addition of glycerol was stopped when the wet weight of the fungal cells was 210 g/L. At this time, the fermentation culturing time was 17 hrs. After the glycerol was depleted, methanol was added in a fed-batch mode, the process proceeded to a methanol-induced culture stage, and sodium pyruvate was added in one portion in an amount of 1 g/L. The rotation speed, the air flow rate and the fed-batch addition rate of methanol were adjusted to allow the dissolved oxygen (DO) to reach >20%. After 96 hrs of induced fermentation, the fermentation was completed. The fermentation liquid was collected, and the supernatant of the fermentation liquid was obtained by centrifugation. The final concentration of the recombinant human collagen is 17.5 g/L as detected by HPLC. The fermentation period is 113 hrs, and the fermentation production level is 0.155 g/L·h, which is 33.6% higher than that of the control group.

Example 7

Fermentation medium: 85% $H_3PO_4$ 6.6 mL/L; $CaSO_4.2H_2O$ 0.3 g/L; $K_2SO_4$ 4.5 g/L; $MgSO_4.7H_2O$ 3.7 g/L; KOH 1 g/L; glycerol 10.0 g/L; and PTM1 0.435 mL/L.

A seed culture was added to a 1000 L fermentor containing 500 L of a fermentation medium at an inoculation amount of 10%, the initial stirring speed was 200 rpm, the fermentor pressure was 0.05 MPa, and the air flow rate and the stirring speed were adjusted so that the dissolved oxygen (DO) was >30%. When the carbon source was depleted, the dissolved oxygen rose sharply. 50% glycerol was added in a fed-batch mode, and the carbon source was supplemented. The addition of glycerol was stopped when the wet weight of the fungal cells was 210 g/L. At this time, the fermentation culturing time was 17 hrs. After the glycerol was depleted, methanol was added in a fed-batch mode, the process proceeded to a methanol-induced culture stage, and sodium pyruvate was added in one portion in an amount of 1 g/L. The rotation speed, the air flow rate and the fed-batch addition rate of methanol were adjusted to allow the dissolved oxygen (DO) to reach >20%. After 96 hrs of induced fermentation, the fermentation was completed. The fermentation liquid was collected, and the supernatant of the fermentation liquid was obtained by centrifugation. The final concentration of the recombinant human collagen is 17.1 g/L as detected by HPLC. The fermentation period is 113 hrs, and the fermentation production level is 0.151 g/L·h, which is 30.2% higher than that of the control group.

Comparative Example

The fermentation medium is a basal salt medium (BSM, see CN102443057B): 85% H3PO4 26.7 mL/L; CaSO4.2H2O 1.175 g/L; K2SO4 18.2 g/L; MgSO4.7H2O 14.9 g/L; KOH 4.13 g/L; glycerol 40.0 g/L; and PTM1 4.35 mL/L.

A seed culture was added to a 1000 L fermentor containing 500 L of a fermentation medium at an inoculation amount of 10%, the initial stirring speed was 200 rpm, the fermentor pressure was 0.05 MPa, and the air flow rate and the stirring speed were adjusted so that the dissolved oxygen (DO) was >30%. When the carbon source was depleted, the dissolved oxygen rose sharply. 50% glycerol was added in a fed-batch mode, and the carbon source was supplemented. The addition of glycerol was stopped when the wet weight of the fungal cells was 218 g/L. At this time, the fermentation culturing time was 16 hrs. After the glycerol was depleted, methanol was added in a fed-batch mode, and the process proceeded to a methanol-induced culture stage. The rotation speed, the air flow rate and the fed-batch addition rate of methanol were adjusted to allow the dissolved oxygen (DO) to reach >20%. After 120 hrs of induced fermentation, the fermentation was completed. The fermentation liquid was collected, and the supernatant of the fermentation liquid was obtained by centrifugation. The final concentration of the recombinant human collagen is 15.8 g/L as detected by HPLC. The fermentation period is 136 hrs, and the fermentation production level is 0.116 g/L·h.

The invention claimed is:
1. A fermentation process for increasing the production level of a recombinant human collagen, comprising:
    inoculating a sterilized fermentation medium with a *Pichia* yeast solution; culturing the fermentation medium for 14-18 hours;
    adding methanol to the fermentation medium to provide a methanol-induced expression stage, wherein the *Pichia* yeast expresses the recombinant human collagen; and
    adding sodium pyruvate to the fermentation medium during the methanol-induced expression stage, wherein the amount of the sodium pyruvate added is 0.01-10 g/L, and wherein the *Pichia* yeast expresses the recombinant human collagen,
    wherein the recombinant human collagen is produced at higher levels than a process where sodium pyruvate is not added to the fermentation medium during the methanol-induced expression stage.

2. The fermentation process according to claim 1, wherein the amount of the sodium pyruvate added is 0.1-1 g/L.

3. The fermentation process according to claim 1, wherein the sodium pyruvate is added in a fed-batch mode.

4. The fermentation process according to claim 1, wherein the fermentation medium of the *Pichia* yeast has a composition comprising 6.6-26.7 mL/L of an 85% aqueous solution of $H_3PO_4$, 0.3-1.175 g/L of $CaSO_4 \cdot 2H_2O$, 4.5-18.2 g/L of $K_2SO_4$, 3.7-14.9 g/L of $MgSO_4 \cdot 7H_2O$, 1.0-4.13 g/L of KOH, 10.0-40.0 g/L of glycerol, and 0.435-4.35 mL/L of a PTM1 solution.

5. The fermentation process according to claim 1, wherein in the fermentation process, the *Pichia* yeast solution is inoculated in an amount of 8-12%, the fermentation temperature is 28-30° C., the pH is adjusted to 5.0-5.2 with aqueous ammonia, the dissolved oxygen is not less than 20%, and the induction time with methanol is 90-120 hrs.

6. The fermentation process according to claim 2, wherein the sodium pyruvate is added in a fed-batch mode.

\* \* \* \* \*